United States Patent [19]

Wiles

[11] Patent Number: Plant 6,633

[45] Date of Patent: Feb. 28, 1989

[54] ACHIMENES PLANT NAMED PINK ROSE

[75] Inventor: Linda S. Wiles, Greenwood, S.C.

[73] Assignee: Geo. W. Park Seed Co., Inc., Greenwood, S.C.

[21] Appl. No.: 103,034

[22] Filed: Sep. 30, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Achimenes plant named Pink Rose.

2 Drawing Sheets

The present invention comprises a new and distinct cultivar of Achimenes plant, hereinafter referred to by the cultivar name Pink Rose.

Pink Rose is a product of a planned breeding program which had the objective of creating new Achimenes cultivars having superior vigor, good branching habits, suitability for pot plants or hanging baskets, double flowers 2" or more in diameter and of various colors, early-flowering, floriferousness, and a long flowering season. Such traits in combination were not present or needed improvement in previously available commercial cultivars of this type.

Pink Rose was originated from a hybridization made in a controlled breeding program in Greenwood, S.C. in 1984. Both the male and female parent were identified by the breeding number 840942-1, with the female parent being selfed from the male parent.

Pink Rose was discovered and selected as one flowering plant within the progeny of the stated percentage by Linda Saussy Wiles on Aug. 21, 1985, in a controlled greenhouse environment in Greenwood, S.C.

Asexual reproduction of the new cultivar by rhizomes, as performed initially by Linda Saussy Wiles at Greenwood, S.C. has demonstrated that the combination of characteristics as herein disclosed for Pink Rose are firmly fixed through successive generations of asexual reproduction.

Pink Rose has not been observed under all possible environmental conditions. The phenotype may vary significantly with variations in environment such as temperature, light intensity, and day length. The following observations, measurements, and comparisons describe plants grown in Greenwood, S.C. under greenhouse conditions which approximate those generally used in commercial practice.

The following traits have been repeatedly observed and are determined to be basic characteristics of Pink Rose, which in combination distinguish this Achimenes as a new and distinct cultivar:

(1) The flowers are double in form and 1.7" to 2.0" in diameter. There are five (5) full size petals and 5 to 9 or more smaller petals measuring 0.7"×0.7" or more when fully expanded.

(2) The upper surface flower color of the outer petals is an attractive Light Pink with the petals showing Silver White on the reverse or underside. Under stress conditions, double petals may retract somewhat into the throat showing very small area of HCC 601-3 Primrose Yellow, with 5 lines and (not too many) dots of HCC 27 Magenta also being apparent.

(3) Generally, two to three flowers appear at each node. Plants are erect when young, and semi-trailing towards end of growing season.

(4) Rhizomes start growing early, producing plants rapidly. From rhizomes planted in early April, flowering plants were available by mid-June.

(5) Plants continue to flower well into late November.

(6) Highly floriferous flowering habit.

Of the many commercial cultivars known to the present inventor, the most similar in comparison to Pink Rose is Blue Rose, disclosed in U.S. Plant Pat. No. 5,919. Reference is made to attached Chart A which compares certain characteristics of Pink Rose to those same characteristics of Blue Rose.

The accompanying color photographic drawings show typical inflorescence and foliage characteristics of Pink Rose, with the colors being as nearly true as possible with illustrations of this type. Sheet 1 is a perspective view of the plant, and sheet 2 comprises a greatly enlarged photo of a single flower and surrounding foliage.

In the following description, color references are made to the Horticultural Colour Chart (HCC), or to The Royal Horticultural Society Colour Chart (RHS) where indicated. The color values were determined between 2:00 pm. and 3:00 pm. on Sept. 23, 1986 under 2200 foot candles of light intensity at Greenwood, S.C.

Classification:

A. *Botanical.*—Achimenes hybrid., cv. Pink Rose.

B. *Commercial.*—Achimenes.

PLANT

A. General appearance:

*Height.*—Erect when young; semi-trailing later.

*Growth.*—Bushy.

*Internode.*—Distance ¾"-1" (1.9 cm to 7.5 cm).

B. Foliage:

*Leaves.*—Numerous.

*Shape.*—¾"×1¾" to 1"×2¼" (1.9 cm by 4.4 cm to 2.5 cm by 5.7 cm.

*Appearance.*—Serrated.

*Color.*—Top side Parsley Green HCC 0962. Bottom side Pod Green-Parsley Green HCC 06⅓×096⅔.

*Texture.*—Pubescent on both upper and lower surfaces, though much reduced on lower surface.

C. Flowers:

*Borne.*—2–3 flowers per node at most nodes, usually 3.

*Type of stems.*—Short.

*Number of flowers per stem.*—One.

*Quantity of blooms.*—Abundant.

D. Blooms:

*Size.*—1.7" to 2.0" (4.3 cm to 5.1 cm).

*Petalage.*—Double, five (5) full size outer petals and 5–9 or more smaller inner petals.

*Shape.*—Approximately round.

*Color.*—Outside petals, upper surface Fuchsine Pink HCC 627/3 with 627/1 mid-veins and few or no other veins, under surface Silver White. Inner petals, upper surface Fushsine Pink HCC 627/3. If inner petals retract then slight White Yellow cast at very center is partially visible with HCC 601-3 Primrose Yellow, with lines and/or dots of HCC 27 Magenta.

E. Reproductive organs:

*Stamens.*—0–5, usually staminode.

*Filaments.*—4–5, sometimes attached to petals.

*Anthers.*—Rare, 0–4.

*Pollen.*—Very rare.

*Pistils.*—1, Deformed.

*Styles.*—Very short, deformed.

*Seed.*—Will not normally produce seed.

Disease resistance: No known disease problems on plants.

CHART A

| CHARACTERISTIC | BLUE ROSE | PINK ROSE |
|---|---|---|
| Smaller petals | 4–6, 0.6" × 0.6" | 5–9, 0.7" × 0.7" |

CHART A-continued

| CHARACTERISTIC | BLUE ROSE | PINK ROSE |
|---|---|---|
| Leaf size | 1.0" × 1.7"–2.5" | 0.8" × 1.8" to 1.0" × 2.3" |
| Leaf color | NCC 0962 Parsley Green with HCC 061/3 Pod Green reverse | HCC 0962 Parsley Green with 061/3 × 0962/3 Pod Green-Parsley Green reverse |
| Internode spacing | 0.7"–1.2" | 0.8"–1.0" |
| Flowers per node | 2–3 | usually 3, sometimes 2 |
| Stamens | 0–4 | 0–5, usually staminode |
| Filaments | 4, sometimes attached to petals | 4–5, sometimes attached to petals |
| Anthers | variable, 0–4 | rare, 0–4 |
| Pollen | some on occasion | some on occasion |
| Pistils | 1 | 1, deformed |
| Styles | 1, normal | 1, very short, deformed |
| Flower color | HCC 40/2 Hyacinth Blue with Silver White reverse; if petals retract, HCC 601/3 Primrose Yellow and HCC 28 Fuschia Purple lines and dots are visible in throat | HCC 627/3 Fushsine Pink with HCC 627/1 mid-veins and few or no other veins with Silver White reverse; if petals retract, slight White-Yellow cast at center (HCC 601/3 Primrose Yellow) and HCC 27 Magenta lines and dots are visible in throat |

I claim:

1. A new and distinct cultivar of Achimenes plant named Pink Rose, as illustrated and described.

* * * * *

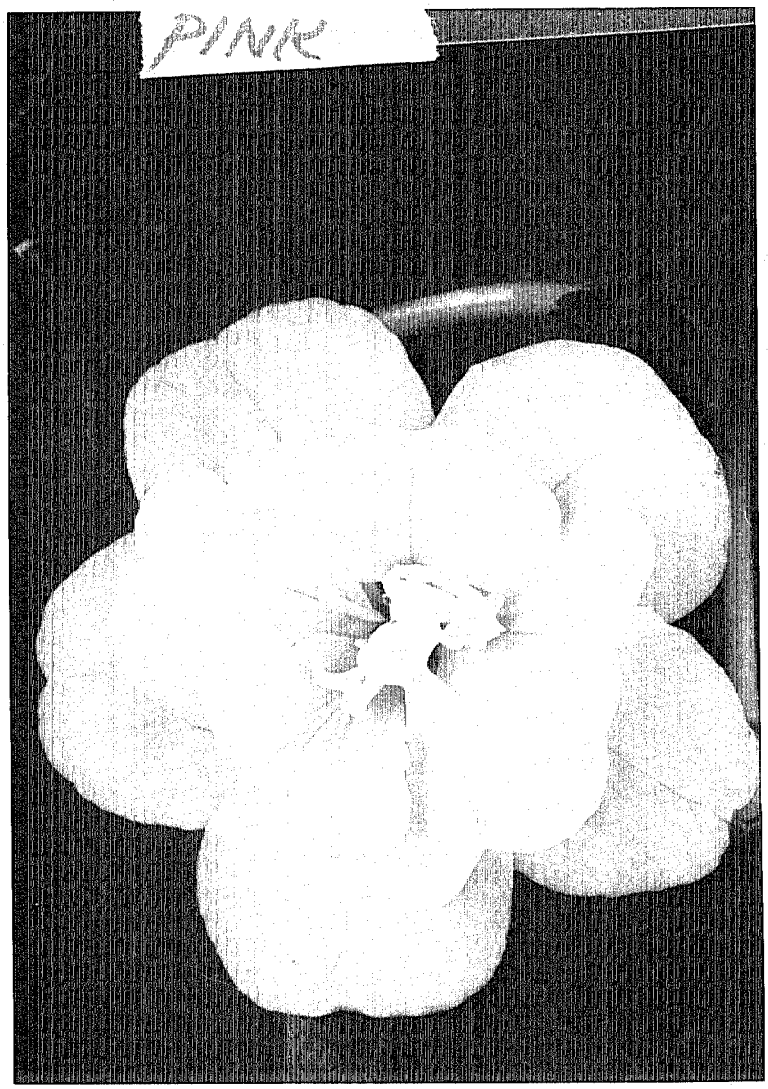
PINK

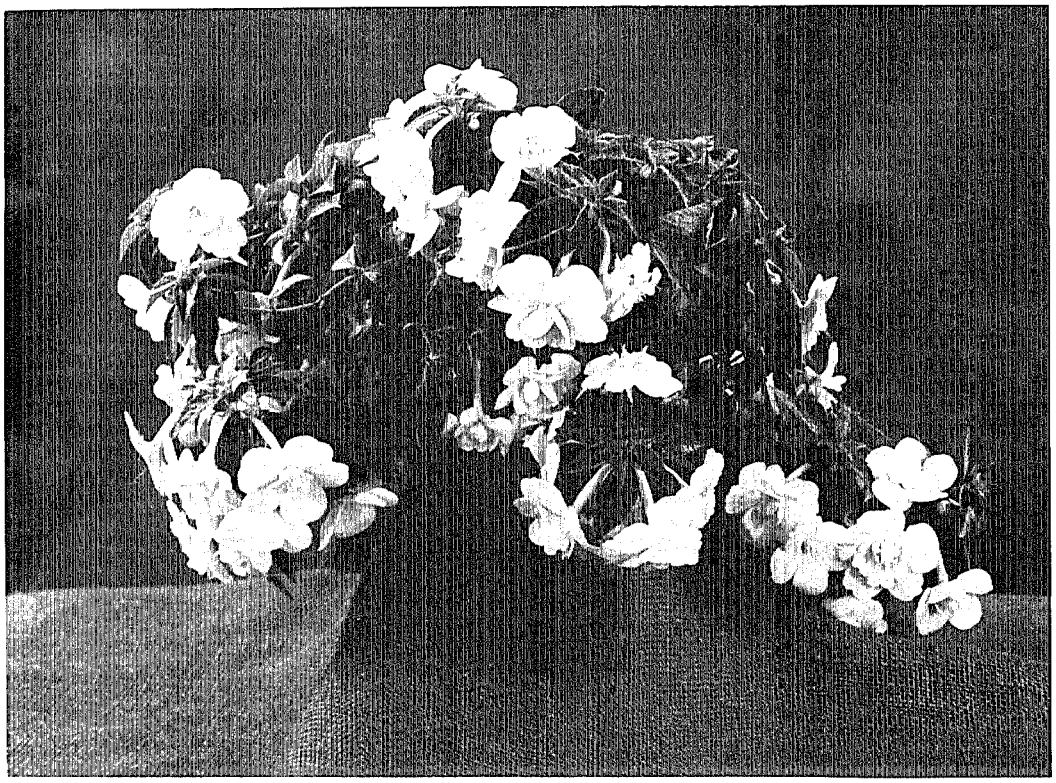

UNITED STATES PATENT AND TRADEMARK OFFICE

CERTIFICATE OF CORRECTION

PATENT NO. : Plant 6,633

DATED : February 28, 1989

INVENTOR(S) : Linda S. Wiles

It is certified that error appears in the above-identified patent and that said Letters Patent is hereby corrected as shown below:

In Column 2, lines 19-22, the final two sentences of the paragraph should read:

> Sheet 1 comprises a greatly enlarged photo of a single flower and surrounding foliage. Sheet 2 is a perspective view of the plant.

In Column 4, CHART A, referring to the CHARACTERISTIC "Pollen", under the column PINK ROSE:

> "some on occasion" should read: "very rare"

Signed and Sealed this

Second Day of January, 1990

*Attest:*

JEFFREY M. SAMUELS

*Attesting Officer*

*Acting Commissioner of Patents and Trademarks*